United States Patent [19]

Brysk

[11] Patent Number: 5,334,527
[45] Date of Patent: Aug. 2, 1994

[54] EPIDERMAL GRAFT SYSTEM

[75] Inventor: Miriam M. Brysk, Galveston, Tex.

[73] Assignee: Board of Regents, The University of Texas System, Austin, Tex.

[21] Appl. No.: 672,840

[22] Filed: Mar. 21, 1991

Related U.S. Application Data

[60] Division of Ser. No. 153,957, Feb. 9, 1988, Pat. No. 5,015,584, which is a continuation-in-part of Ser. No. 108,338, Oct. 14, 1987, abandoned.

[51] Int. Cl.⁵ ............................ C12N 5/00; A61F 2/10
[52] U.S. Cl. ........................... 435/240.23; 435/240.2; 435/240.243; 623/15
[58] Field of Search ................ 435/240.23, 240.243, 435/240.2, 240.21, 1; 623/15

[56] References Cited

U.S. PATENT DOCUMENTS

| | | | |
|---|---|---|---|
| 3,883,393 | 5/1975 | Knazek et al. | 435/240.242 |
| 4,060,081 | 11/1977 | Yannas et al. | 623/11 |
| 4,087,327 | 5/1978 | Feder et al. | 435/240.241 |
| 4,220,725 | 9/1980 | Knazek et al. | 435/285 |
| 4,254,226 | 3/1981 | Eisinger et al. | 435/240 |
| 4,296,205 | 10/1981 | Verma | 435/285 |
| 4,299,819 | 11/1981 | Eisinger | 424/574 |
| 4,308,351 | 12/1981 | Leighton et al. | 435/284 |
| 4,399,123 | 8/1983 | Oliver et al. | 424/94 |

(List continued on next page.)

FOREIGN PATENT DOCUMENTS 0242270 10/1987 European Pat. Off. .

OTHER PUBLICATIONS

Kitano and Endo, Biochemistry of Cutaneous Epidermal Differentiation, Ed. by Seiji, et al., University Park Press, pp. 319-335 (1977).

Pittelkow, Mayo Clin. Proc, 61:771-777 (1986).
The Lancet, "Culture Crafts of Keratinocytes: A Growth Industry?" p. 783, Apr. 5, 1986.
Thivolet, et al, Transplantation, 42:27.
Dermatology Perspectives, Ed. by Gahagan, "Synthetic dressings speed healing and reduce pain" pp. 2-3 (1986).
Eaglstein, J. of Am. Acad. Dermatol., 12:434-440 (1985).
Eisinger, et al., Surgery, pp. 287-293 (1980).

(List continued on next page.)

Primary Examiner—Douglas W. Robinson
Assistant Examiner—Susan M. Dadio
Attorney, Agent, or Firm—Arnold, White & Durkee

[57] ABSTRACT

The present invention involves a readily produced skin autograft or silograft composite suitable for the supplementation or replacement of injured skin. A sheet of collagen-coated pliable material such as synthetic surgical dressing is used as a foundation for the skin autograft composite. The synthetic surgical dressing, if not pre-coated with collagen, may be placed in a container and coated with collagen. Epidermal cells, preferably obtained from a prospective recipient of the skin autograft composite being produced, are cultured in an appropriate medium substantially preventing cell differentiation to form epidermal cells on the surface of a collagen-coated container. When substantially confluent, the epidermal cells are enzymatically detached from the culture vessel and layered upon a collagen coated desiccated surgical dressing infused with low calcium culture medium. In actual use, the skin autograft composite is inverted, placed on a recipient, and allowed to remain in position until epidermal cells attach to the recipient and facilitate the formation of a skin-like covering.

14 Claims, No Drawings

U.S. PATENT DOCUMENTS

| | | | |
|---|---|---|---|
| 4,485,096 | 11/1984 | Bell | 424/95 |
| 4,495,288 | 1/1985 | Jarvis, Jr. et al. | 435/241 |
| 4,504,547 | 3/1985 | Horodniceau et al. | 428/407 |
| 4,533,635 | 8/1985 | Guédon born Saglier et al. | 435/240.241 |
| 4,539,716 | 9/1985 | Bell | 623/1 |
| 4,769,317 | 9/1988 | Hefton | 435/240.25 |
| 5,000,963 | 3/1991 | Hefton | 435/240.23 |
| 5,015,584 | 5/1991 | Brysk | 435/240.23 |

OTHER PUBLICATIONS

Gallico, et al., The New England Journal of Medicine, 311:448–51.

Green, et al., Proc. Natl., Acad. Sci, U.S.A., 76:5665–5668 (1979).

Boyce, et al., J. Tissue Culture Methods, vol. 9, No. 2, 1985, pp. 83–93.

Biomaterials, vol. 6, No. 4, Nov. 1985, Butterworth & Co. Ltd., K. J. Quinn et al.

La Recherche, vol. 14, No. 141, Feb. 1983, (Paris, FR), C. Tutin.

WO, A 83/01385 (Massachusetts Institute of Technology), Apr. 28, 1983.

WO, A, 83/01384 (Massachusetts Institute of Technology), Apr. 28, 1983.

International Search Report.

Rheinwald and Green, Cell, 6:311–344 (1975).

EPIDERMAL GRAFT SYSTEM

This application is a division of application Ser. No. 07/153,957, filed Feb. 9, 1988, now U.S. Pat. No. 5,015,584, which is a continuation-in-part of application Ser. No. 07/108,338, filed Oct. 14, 1987, now abandoned.

BACKGROUND OF THE INVENTION

The present invention relates to a skin autograft composite comprising human epidermal cells and usable, for example, in the treatment of burn victims. Effective and readily usable methods for treating substantial injuries to skin have long been goals of physicians and scientists alike. Extensive dermal injury is most frequently caused by burns. With severe burns the epidermal and dermal skin structures in particular areas may be so severely damaged that no epidermal cells remain to repopulate as skin. While numerous skin substitutes such as pigskin, for example, have been tried as coatings for burn wounds, none has proved satisfactorily effective.

Many efforts have been made to facilitate the regrowth of epidermal cells on areas denuded of native skin structures. Because of individual immunological characteristics, the utilization of a burn victim's own epidermal cells to create a new skin covering has been accepted as an ideal potential remedy for such skin injuries. A skin autograft comprising an epidermal cell population would constitute such a new skin covering or an initiation of the regrowth leading to a natural skin substitute. The preparation of an epidermal cell population for purposes of autograft formation may involve in vitro cell culture and possibly an extensive expansion in the number of desired cells.

Human diploid epidermal cells have been grown in culture in the presence of fibroblasts. However, proliferation of fibroblasts must be controlled so that the epidermal cell population is not overgrown. This requires plating epidermal cells with irradiated 3T3 (mouse) cells. Rheinwald and Green, Cell. 6, 331-334, November 1975. This technique also requires the presence of dermal components and cell culture to full differentiation. Despite these limitations, which the yield far from optimal, it has been used for grafts on burn patients.

Kitano et al. suggest that keratinocytes dispersed from epidermis grow without dermal components in a suitable culture medium (30% fetal bovine serum) and show some signs of differentiation (Biochemistry of Cutaneous Epidermal Differentiation, Ed. by Seiji etal. University Park Press, 1977, pp. 319-335). However, this technique has not solved the skin autograft problem.

Approaches to the use of epidermal cells cultured and expanded in vitro and used as skin autografts are included in U.S. Pat. Nos. 4,254,226 and 4,299,819. These references describe processes generally involving: separation of the epidermis from the dermis in samples of human skin; dissociation of the epidermis into epidermal cells; growth of the epidermal cells into a pure epidermal sheet in a tissue culture medium without dermal components and having a pH of from about 5.6 to about 5.9; and application of the resultant epidermal cell sheet to an afflicted area of a burn victim.

Certain earlier efforts generally related to objects of the present invention may be described as follows:

Knazek etal. (U.S. Pat. Nos. 3,883,393 and 4,220,725) describe a system that is to grow cells as three-dimensional structures in semi-permeable tubes. Epidermal undifferentiated basal cells do not grow as three-dimensional structures but instead as a monolayer. (Cancerous epidermal cells grow as undifferentiated three-dimensional structures; indeed this is a standard test for neoplasia). Cells growing inside a capillary tube do not constitute a suitable material for a skin graft.

Feder etal. (U.S. Pat. No. 4,087,327) describe a geometrically complex analog of the Knazek system. The same comments apply.

Verma (U.S. Pat. No. 4,296,205) describes a system for continuous growth of a limited number of cells by the continuous dialysis of the culture media. Epidermal cells in such a system would differentiate and die and are, therefore unsuitable as a graft.

Jarvis et al. (U.S. Pat. No. 4,495,288) describe a culturing system of anchorage dependent cells in suspension. Epidermal cells will not grow in suspension.

Leighton etal. (U.S. Pat. No. 4,308,351) describe a system designed for the growth of pathological and cancer cells. The cells were nurtured through a semi-permeable membraneous wall.

Oliver etal. (U.S. Pat. No. 4,399,123) describe fibrous tissue (dermis) preparations for transplantation. Epidermis is not a fibrous tissue. The present invention involves an intact cell layer of epidermal cells.

Bell (U.S. Pat. Nos. 4,485,096 and 4,539,716) and Yauas et al. (U.S. Pat. No. 4,060,081) describe synthetic skin substitutes. These may be alternatives to grafting but they are unrelated to the autografts of the present invention.

Eisinger (U.S. Pat. No. 4,299,819) and Eisinger etal. (U.S. Pat. No. 4,254,226) describe fully differentiated epidermal cells in a low pH culture medium. To use these cells as grafts, they were attached to the dermal side of pig skin or a collagen sponge and then used this sticky covering to yank the cultured cells loose from their attachment to the culture vessel. In this fully differentiated system there could have been but few dividing cells (undifferentiated) altogether, and many no doubt were lost or damaged during any transfer process onto a wound.

In the usual procedures used by other laboratories, the epidermal cells are fully differentiated. They are lifted by yanking from the culture vessel or are detached enzymatically by dispase. The cells in the latter procedure shrink to about one-half their surface area. These procedures are needed in order to protect the structural integrity of the cells used for a graft.

Where an individual has had extensive skin damage, for example from burns, a graft may be immunologically rejected unless the cells being grafted are from the same individual. To expand the available epidermis, epidermal cells may be grown in culture and then used as grafts.

Technical transfer difficulties such as those involved in detaching cells from culture vessels, spreading them over the wound and providing them with appropriate dressings have impeded rapid and effective treatment of dermatological injuries. Enzymatic detachment of cultured epidermal cells from cell culture vessels, for example, has resulted in up to 75% shrinkage while mechanical transfer (picking up the cells on a rigid artificial structure and then loosening them at the wound) has resulted in substantial cell loss and damage.

The above designated and other analogous known methods of skin autografting may represent progress in the field but have not proven completely satisfactory. Problems unsolved by these earlier methods include: insufficient number of undifferentiated epidermal cells for grafting; difficulties in the removal of an epidermal sheet from a tissue culture container; shrinkage and partial destruction of the epidermal sheet; paucity of viable epidermal cells; and a lack of a sound and physiologically acceptable graft covering. The processes of the present invention permit these and other related problems to be minimized or solved.

SUMMARY OF THE INVENTION

The present invention involves a process for preparation and emplacement of a skin autograft. The process, in one embodiment, comprises: the culture and subculture of donor epidermal cells in a medium in which the cells are maintained in an undifferentiated state; the attachment of the cultured cells to a specially pretreated synthetic surgical dressing; the emplacement of the cells-dressing composite upon the graft site; and the growth of the grafted cells under the protection of the dressing, which is shed upon the completion of the healing process. Enzymatically-dispersed epidermal cells are anchored on collagen and grown in a low calcium medium which inhibits differentiation. A surgical dressing is modified by desiccation, collagen-coating and infusion of growth medium (supplemented with growth factors, hormones and antibiotics); cells will not attach to the dressing without such a pretreatment. Enzymatically-detached cultured cells are seeded onto the conditioned dressing. As soon as the cells become attached, the composite of cells and dressing is transferred to the graft site (with the cells in contact with the wound) and left there. The cells emplaced on the graft are still undifferentiated; they are thus all mitotic and have not yet established a polarity. Once they are anchored to the graft site, the cells divide and differentiate with the proper polarity (towards the outside). As the wound heals, the differentiated cells in contact with the dressing slough off, leaving the dressing detached.

In the system of the present invention, a mobile substratum is used comprising a surgical dressing whose properties have been altered by coating with matrix proteins (for superior cell attachment) and desiccated, so as to allow the infusion of media, antibiotics and growth factors (all important in feeding the graft and the wound site). Once emplaced, the substratum protects the integrity of the graft and sustains it. Without the pretreatment of the surgical dressing the cells will not attach to it.

Pliable materials usable in the practice of the present invention are durable and most preferably semipermeable membranes. A synthetic surgical dressing most preferably used in the practice of the present invention is a membrane comprising polyethylene oxide/water such as that sold under the name VIGILON by Bard Home Health Division, C. R. Bard, Inc. Berkeley Heights, N.J. A translucent or transparent, rather than a substantially opaque synthetic surgical dressing is most conveniently used in the process of the present invention. Such translucency or transparency simplifies observation of the extent of epidermal cell growth or confluency.

Synthetic surgical dressings generally useful in the compositions and processes of the present invention may comprise membranous polyurethane, polyethylene oxide/water, hydrocolloid, silicone/nylon or monofilament nylon, for example. Examples of commercially available synthetic polyurethane surgical dressings include those sold under the tradenames: OP-SITE, EN-SURE, TEGADERM, ACCUDERM and BIOCLUSIVE. An example of a commercially available synthetic polyethylene/water surgical dressing is that sold under the tradename: VIGILON. Such synthetic polyethylene/water surgical dressings usually are a layer of hydrogel between two polyethylene sheets. One polyethylene sheet is usually removed and the hydrogel layer applied to skin wounds. Examples of commercially available synthetic hydrocolloid surgical dressings include those sold under the tradenames: COM-FEEL ULCUS and DUODERM. An example of commercially available synthetic silicone/nylon surgical dressings is BIORANE which is a silicone membrane bound to knitted nylon and is coated on one surface with collagen peptides. An example of commercially available monofilament nylon surgical dressings is N-TERFACE which is a woven high-density nylon.

Others have used cells that have fully differentiated. This was done to protect the integrity of the epidermal cells during the transfer process to the wound. However, differentiated cells cannot divide, so that most of what was put on the wound did not contribute to the regrowth process. Here, since the substratum is providing the structural integrity, we are able to transfer undifferentiated cells to the graft.

The treatment of a split-thickness skin section with proteolytic enzyme results in separation of dermis from epidermis. The process preferably further involves the formation of a cellular suspension from the enzyme-treated epidermis. Dissociated epidermal cells are separated from the epidermal cellular suspension. The detached epidermal cells as well as minced dermis are washed with eucaryotic medium containing 10% FCS then transferred to culture.

Vessels are precoated with either of the following: collagen, fibronectin, or laminen or with a suspension of lethally irradiated 3T3 cells which have been allowed to attach to the culture vessel for about two days. The cells are allowed to attach in MEM containing 10% FCS for 2 hours, thereafter they are grown in MCDB-153 medium, with media changes every two days.

The structure of the epidermis has definite polarity. The basal cells, those adjoining the dermis, are undifferentiated, whereas those cells above are differentiated. In order to achieve an effective skin graft, basal cells must contact the wound; if differentiated cells are placed on the wound then there is no graft face. Once on the wound, the basal cells differentiate into a multi-layered epidermis with the stratum corneum outside. Since the present invention involves placement of undifferentiated cells on the wound, there is no problem with polarity.

On the graft, the culture medium, growth factors and antibiotics infused into the surgical dressing sustain the cells until they can become anchored to the wound. The dressing continues to provide a physical protective barrier for the cells and the wound. As the wound heals, the cells become a multi-layered differentiated epidermis. The outer cells begin to slough off. The surgical dressing above them can then be easily lifted off without damage to the skin.

DESCRIPTION OF PREFERRED EMBODIMENTS

The present invention concerns a unique skin autograft composite in the treatment of skin lesions such as those which may be produced by burns, etasis ulcers, and bullous skin diseases. Epidermal cells are cultured in a medium in which they do not differentiate, detached enzymatically with trypsin, seeded onto a chemically modified surgical dressing (collagen-coated, desiccated, and infused with growth factor supplements and antibiotics). After a cell attachment period of several hours, the cell-dressing composite is transferred to a wound (cell-side down, dressing up).

The transfer is thus carried out with a composite unit possessing structural integrity, so that there is no mechanical or chemical damage to the epidermal cells as a result of the transfer. The synthetic surgical dressing is left as the outer surface of the graft, fulfilling its normal function as a pliable external protective barrier against desiccation and infection.

The epidermis is composed of layers of 4 cell types. Only the basal layer (the bottom layer adjacent to the dermis) is undifferentiated and can undergo cell division, as compared with the other 3 cell layers that are differentiated and cannot divide. In ordinary tissue culture systems, where the cells are allowed to differentiate, it is not advisable to invert the cultured cells as a unit onto a wound because this would place in contact with the wound the top-most layer which consists of differentiated cells. It is, therefore, necessary to rip the cultured cells loose from their attachment so that the bottom layer can be applied to the wound. In this process there is generally much mechanical damage and cellular loss. A key idea involved in the present invention is that the cells are maintained in a low calcium medium in which they do not differentiate, this results in there being dividing cells at the surface. Such maintenance makes it possible to flip the cultured cell layer onto the wound and have a graft that takes. An advantage of the method of the present invention is that the entire unit consisting of the cells, the attachment matrix (e.g. collagen) and the structural base (preferably surgical dressing) may be transferred without significant mechanical stress or loss of cells.

The present invention involves a system for optimally growing epidermal autografts and placing them on a wound. The novelty of the present invention may be best envisioned as including an effective technique for grafting rather than in a method of epidermal tissue culture per se. The disiderata are different from what they would be in continuous cell culture for laboratory study of cells (to which most of the above-referenced patents pertain).

Epidermal cells are dissociated with enzymes (trypsin, dispass and pronase), the enzymes are neutralized with serum and the cells are cultured for 3–4 days in MCDB-153 medium. In this medium the epidermal cells do not differentiate. They are then subcultured on collagen-coated vessels at a cell density of $5 \times 10^3$ cells/cm$^2$. After growth for a week in MCDB-153 medium, the cells are either further subcultured or are used directly to prepare a graft. In preparing the graft, the cells are removed from the culture vessels with trypsin, centrifuged in MEM+10% FCS, then seeded onto a specially treated surgical dressing for 4–6 hrs.

An entire skin autograft composite of collagen-coated pliable material with a layer of substantially confluent epidermal cells is thus produced. Such a skin autograft composite may then be transferred to an area denuded of skin, cell-free side outermost and the epidermal cell layer in contact with the injury. The skin composite is then kept in place, for example by taping, so that epidermal cells may proliferate and attach to the injured skin surface of the patient being treated. This method is relatively fast, the composite being without substantial shrinkage or damage during transfer, and the wound is protected with a surgical dressing under which will grow a natural protective epidermal cell covering.

Producing a skin autograft composite of the present invention initially involves obtaining a pliable material such as a synthetic surgical dressing. The pliable material may be obtained pre-coated with a characteristic animal basement substance, preferably collagen, although it is believed that substances such as laminin, fibronectin or heparan sulfate proteoglycan may also be used. A sample of synthetic surgical dressing, for example, may be coated with an animal basement substance by incubation with a solution of said substance. For purposes of simplicity and because collagen is a preferred basement substance and synthetic surgical dressing is a preferred pliable material, a collagen-coated synthetic surgical dressing will be primarily referenced herein. A collagen-coated synthetic surgical dressing is preferably seasoned by MCDB-153 and then eucaryotic cell growth medium prior to placement on the lower surface of a container or dish suitable for eucaryotic cell culture. Epidermal cells cannot be cultured directly upon the synthetic surgical dressing, but culture can be achieved if the synthetic surgical dressing is first coated with collagen.

In cases where the dressing is to be coated with collagen, a sample of synthetic surgical dressing may be emplaced in container, a thin layer of an aqueous collagen solution may be placed thereupon and evaporation of water permitted to ensue. After at least substantial departure of water, a collagen coating remains on the surface of the synthetic surgical dressing. This drying step is preferably conducted under sterile conditions, for example, during exposure to ultraviolet light, to impede bacterial contamination.

The epidermal cells are minimally allowed to attach and may even be cultured to reach a state of substantial confluency on collagen-coated synthetic surgical dressing to produce a preferred skin autograft composite of the present invention. In the case where a burn victim awaits treatment, the skin autograft composite may be inverted and placed on an appropriately prepared injured area bereft of or deficient in healthy skin tissue. The surface of the synthetic surgical dressing without epidermal cells presents an external surface and the epidermal cell layer contacts the injured area. The skin autograft composite should be retained in position for at least a week to permit the spread of epidermal cells to the injured area. When the synthetic surgical dressing is eventually removed, a cellular epidermis precursor is in place and will proceed to repopulate the area for skin normalization. With a mobile substratum, differentiated cells were not required for the maintenance of graft structural integrity. Undifferentiated cells characteristically exhibited growth and cell division. A medium with low calcium ion concentration was utilized in processes of the present invention to maintain epidermal cells in an undifferentiated state (Hennings et al., Cell, 19:245–254, 1980). With such a medium, MCDB-153

(Boyce et al., J. Invest. Dermatol., 81, Suppl. 335–405, 1983) for example, epidermal cells were cultured and subcultured at low seeding densities ($5 \times 10^3$ cells per $cm^2$ area of the culture vessel). In going from fresh tissue to the primary culture, the initial cell attachment was slow (3–4 days). It was found that attachment could be achieved in a single day by using a medium composed of equal volumes of MCDB-153 and MEM containing 10% fetal calf serum, after which MCDB-153 medium alone could be used.

Given the capacity to properly subculture epidermal cells, a substratum suitable for grafting is only necessary in the final passage. Prior passages may equally well be carried out, for example, on collagen-coated culture dishes or a variety of collagen-coated artificial substrata.

With a low calcium, differentiation-inhibiting medium and with collagen coating of substrata (both are preferred) cells may be attached and grown directly on surgical dressing. Commercially available surgical dressings are preferred substrata for practice of the present invention. With one such dressing (Vigilon), for example, after coating with collagen and using MCDB-153 medium for cell culture, effective skin autografts were readily produced. Cells grown on culture vessels (or on the mobile substrata just described) are fed from above, whereas in natural epidermis they are fed from the underlying dermis. Natural feeding conditions were more closely mimicked by pretreatment of the surgical dressing as described herein. When the collagen-coated Vigilon dressing was dried 2–3 hrs under U-V light, it lost its gelatinous consistency and shrank. When cell culture medium was then added to the dried dressing, the dressing rehydrated in a sponge-like fashion, absorbing medium to form a preferred substratum. When subcultured epidermal cells were plated on this substratum, they completely attached and spread after only 4–6 hours, doing as well as cells which were plated on cultured vessels did only after two days. Because there was no lag time during the process of attachment, the cells started to multiply almost immediately.

As mentioned earlier herein, the epidermis is composed of four layers of distinct cell types. Only cells of the basal undifferentiated layer (the bottom layer adjacent to the dermis) can undergo mitosis and grow in tissue culture. The other cell layers are differentiated and cannot grow. All the earlier existing tissue-cultured epidermal graft systems require fully differentiated cells. For suitable grafts, the cultured and fully differentiated cells must be transferred as a cohesive unit onto a graft site. The cells are detached from culture vessels either mechanically or by enzymatic detachment. This method has disadvantages including shrinkage of the cohesive unit, highly differentiated cells of limited growth potential, and mechanical weakness and fragility of the loosened layers of cells. In these other graft systems, long culture times are needed for cell expansion and cell differentiation and the final graft contains relatively few undifferentiated basal cells available for cell division. In the culture system according to the methods of the present invention, the cells are grown in media low in alkali-earth metals, particularly calcium, in which they do not differentiate and continue to divide. These cells can be further expanded by subculturing in low-calcium media containing a variety of growth-related factors (e.g. epidermal growth factor, insulin, hydrocortisone, cholera toxin, ethanolamine, phosphoethanolamine and extracts from serum or pituitary or other tissues).

In a last step characterizing the in vitro epidermal cell culture system of the present invention, the cultured cells are seeded in tissue culture medium onto a synthetic surgical dressing coated with dermal matrix protein such as type-I collagen, laminin or fibronectin. The cells rapidly become anchored to this base and spread on it. The whole structure is then lifted from the containing vessel and inverted onto the graft site. This is feasible because the cells are firmly attached but have been kept undifferentiated so that those cells coming into contact with the wound are mitotic (differentiated cells in an outer layer would interfere with adhesion to the wound). Transfer onto the graft site occurs without cell damage or shrinkage, mitotic cells come in contact with the wound for more rapid reepithelialization, and the graft is provided with an appropriate protective dressing; all in the same step.

The polyethylene oxide (or other) synthetic surgical skin dressing is coated with type I collagen (or other dermal matrix proteins), dried, then rehydrated in culture medium. It is then layered with subcultured epidermal cells. After the cells have become adherent and have spread, they are then applied as a graft (described above).

Prior to the placing of the graft, the wound area is preferably lightly coated with type I collagen. The graft cells quickly anchor and proceed to spread and grow. Because the graft emplacement does not require suturing, reepithelialization occurs without scarring.

This technique has also been successfully used to emplace an autograft on a vitiligo patient because both pigmented melanocytes and epidermal cells grow in the present culture system. Vitiligo is successfully treated. After two weeks, the graft had completely taken, the skin was fully reepithelialized and differentiated and there was no scarring. The Vigilon synthetic surgical dressing sloughed off after two weeks. To date, there have been five successful treatments.

The present culture system is also being applied to provide grafts for stasis ulcers. Such grafts provide rapid pain relief, elimination of infection, and are cosmetically pleasing. The treatment has been successful with the first two patients.

The greatest need for autografts involves patients with extensive burns. A rapid graft covering protects victims from pain, infection, and desiccation while providing growing cells for reepithelialization. The system of the present invention provides a rapid cell expansion in culture and prompt coverage with mitotic cells capable of rapid would coverage.

It is anticipated that the present graft system may also be used for skin replacement after surgical removal of skin or mucosal cancers. After surgery for cancer of the oral mucosa, current practice is to use whole skin for autografts. This consists of epidermis as well as dermis containing root hairs and other dermal glands. With the culture system of the present invention, the graft will consist of only epidermal basal cells. The undifferentiated cells, when they are emplaced on an oral mucosa, are expected to partially differentiate into an oral type of tissue mucosa, and not into an epidermis with a stratum cornsum.

The culture system of the present invention provides grafts which reepithelialize smoothly without scarring. This of particular interest to plastic surgeons for the avoidance of or repair of scars. The success with Vitiligo suggests the possibility of repigmenting skin regrowth on former burn victims.

Skin allografts may be rejected because they contain Langerhans cells and other class II antigen-presenting cells. Epidermal cells continued in tissue culture have been reported to become devoid of these cells. Thus there is the likelihood of successfully using the epidermal grafts of the present invention as immunotolerated allografts for wound coverage. If such cultured cell allografts are not rejected, then there should be available an abundant supply of cells for grafting on burn patients who have insufficient intact skin of their own to donate for autograft formation. Furthermore, because there is no need to wait for a high numerical expansion of the donor epithelial cells, there should be an ability to graft earlier, with obvious medical advantages. When the autografts of the present invention are described herein, it is understood that they may be used as allografts, should antigenicity of cultured epidermal cells be sufficiently suppressed.

A most preferred embodiment of the present invention may be described as follows:

(1) Separating epidermis from dermis by trypsinization;
(2) Mincing the epidermis and dermis;
(3) Centrifuging the minced material in minimal essential medium with 10% serum (the serum neutralizing the trypsin);
(4) Inoculating the centrifuged cells into collagen-coated culture vessels in EMEM:MCDB-153, 50:50, medium. This medium provides the best cell attachment to the culture vessels thus far noted;
(5) The cells are then cultured in the collagen coated culture vessels in MCDB-153 medium until they are substantially confluent;
(6) The cells are then subcultured by detachment with trypsin from culture vessel walls and reinoculation into collagen-coated flasks at a level of 5 times $10^3$ cells-$CM^2$ in EMEM:MCDB-153, 50:50;
(7) Synthetic surgical dressing is cut to fit the shape of a skin or mucosal wound where reepithielization is desired, coated with collagen, dried 2-3 hrs and infused with MCDB-153 medium containing antibiotics;
(8) Epidermal cells are detached from the collagen coated flasks by trypsinization, the trypsin neutralized with EMEM-10% FCS and seeded onto the collagen-coated synthetic surgical dressing in MCDB-153 medium; and
(9) After a 4-6 hr period of cell attachment, the synthetic surgical dressing-epidermal composite may be placed onto the mucosal or skin wound.

These examples are presented to describe specific preferred embodiments and utilities of the present invention and are not meant to limit the present invention unless otherwise stated in the claims appended hereto.

EXAMPLE 1

Synthetic Surgical Dressing Preparation

A synthetic surgical dressing of the polyethylene/hydrocolloid type (VIGILON) was initially cut in a shape to fit a designated wound. One of the two polyethylene surface layers was removed from the surgical dressing and the residue placed on the bottom of a culture container with the hydrocolloid side facing upward and the remaining polyethylene side facing downward. The dressing in the tissue culture dish was covered (ca. 1 mm or less) with a solution comprising about 1 mg collagen/ml (VITROGEN Collagen Corp., Palo Alto, Calif.). A collagen-coated synthetic surgical dressing was then produced after a period of drying with a flow of sterile air and under irradiation with ultraviolet light. The dried collagen coated surgical dressing was rehydrated in MCDB-153 medium and expanded to about double its original thickness.

EXAMPLE 2

Preparation of Epidermal Cells

A split-thickness section of adult human skin obtained from a patient was rinsed in sterile saline. It was then dried on a petri dish, dermis side down, for several hours in a tissue culture hood. The dried section was then lifted and floated on 0.25% trypsin in saline for 1 hr. at 37° C., followed by mincing in EMEM-10% fetal calf serum. The minced epidermis and dermis was harvested by low speed centrifugation and resuspended in plating medium (a 1:1 mixture of EMEM-10% FCS and MCDB-153 medium). The cells were then counted in a hemocytometer and checked for viability by their degree of trypan blue exclusion. Tissue culture vessels were coated with collagen by drying a 1 mg/ml collagen (Vitrogen, Collagen Corporation, Palo Alto, Calif.) solution wetting the walls of the vessels. The collagen-coated vessels were inoculated with $5 \times 10^3$ viable cells/$cm^2$ using epidermal cells from fresh skin samples or from the above described cell suspension in plating medium. After about an initial 2 hr incubation in the plating medium, the medium was changed to MCBD-153 and the cells refed every 2-3 days.

After cell culture for about 4-5 days an approximately 75% cell confluence was reached and the cells of the primary culture were loosened with trypsin and subcultured in uncoated or collagen-coated culture vessels with MCBD-153 medium at a seeding density of $5 \times 10^3$ cells/$cm^2$. The cells were subcultured when they reached 50-75% confluence. These cells in turn, when confluent, were seeded onto the surgical dressing.

EXAMPLE 3

Preparation of a Skin Autograft Composite

Viable epidermal cells from subcultures in collagen-coated vessels (prepared as described in Example 2) were seeded onto synthetic surgical dressing (VIGILON) coated with a thin collagen layer (prepared as described in Example 1). Cells were inoculated in MCBD-153 medium at a density of $5 \times 10^3$-$10^4$ cells/$cm^2$.

EXAMPLE 4

Transplantation of the Skin Autograft Composite onto Patients

After 4-6 hrs, the skin autograft composites of Example 3 comprising synthetic surgical dressing and attached non-differentiated epidermal cells were lifted from the culture vessels and inverted onto patients with wounds.

EXAMPLE 5

Preparation and Use of Human Skin Autograft Composites

The present example concerns a most preferred embodiment of the present invention insofar as its broad applicability to medical problems. The procedures as described above in the body of this application and prior examples were utilized in this procedure unless otherwise specified below.

A sample of fresh human skin was obtained from a patient, trypsinized, and teased to facilitate the separation of epidermis from dermis. The dissociated epidermal cells were separated by centrifugation and any residual trypsin neutralized by washing with EMEM having 10% fetal calf serum. The separated trypsin-neutralized epidermal cells were then suspended in a medium comprising EMEM (with 10% fetal calf serum) and MCDB 153 in a 1:1 ratio. The suspended cells were then distributed in collagen-coated tissue culture vessels and incubated for two hrs under the usual conditions of tissue culture. The EMEM:MCBD medium was replaced with MCBD 153 medium and the cells were grown for 5 to 7 days and refed fresh medium every 2 days. At the end of this period the cells had grown to produce a cell culture which was substantially confluent. The substantially confluent cell culture was then trypsinized by incubation for about 3 minutes with a solution comprising, per liter, 0.5 g trypsin, 0.5 g EDTA, 1.0 g dextrose, 25.8 g sodium bicarbonate, 8.0 g sodium chloride and 24 g potassium chloride. After centrifugation the trypsin was neutralized as before and the cells were seeded onto the modified surgical dressing.

In the meantime, a piece of VIGILON synthetic surgical dressing was coated with collagen and dried for about 3 hours under ultraviolet light to suppress contamination. The dried collagen-coated VIGILON was then rehydrated in MCBD-153 medium containing antibiotics. The collagen-coated and medium-rehydrated piece of surgical dressing was placed in a tissue culture container.

Cells from the subculture were loosened by trypsinization, the trypsin neutralized after centrifugation of the cells, and the cells resuspended in MCDB-153 medium. The resuspended cells were carefully layered on the collagen-coated VIGILON in the tissue culture container and incubated for 4–6 hours. The surface area of the collagen-coated VIGILON was about the same as the surface area of the particular subculture utilized as a source of cells. After 6 hours of incubation the VIGILON material was removed and inverted on skin wounds of several patients as skin autografts. After a period of about 2 weeks the surgical dressing had at least in part sloughed off and was completely removed, if necessary. The dermal surface of each wound site was completely healed and no scarring was apparent.

This example describes the best mode of the invention as presently contemplated. It is to be noted that the MCBD-153 medium impregnated in the synthetic surgical dressing comprises antibiotics and dextrose, both of which are thought to promote wound healing and epidermal cell viability while preventing contamination by microorganisms.

Changes may be made in the ingredients, elements and assemblies described herein or in the steps or the sequence of steps of the method described herein without departing from the concept and scope of the invention as defined in the following claims.

What is claimed is:

1. A skin autograft or allograft composite consisting essentially of:
undifferentiated human epidermal cells attached to a collagen-coated synthetic surgical dressing comprising infused MCDB-153 cell culture medium.

2. The composite of claim 1 wherein the synthetic surgical dressing is membranous polyurethane; polyethylene oxide and water; hydrocolloid; silicone and nylon; or monofilament nylon.

3. The composite of claim 1 wherein the synthetic surgical dressing is membranous polyetehylene oxide and water.

4. The composite of claim 1 wherein the human epidermal cells are obtained by a process including the steps of:
treating a human skin section with an aqueous solution comprising a proteolytic enzyme; and separating epidermal cells from the treated section.

5. The composite of claim 4 wherein the proteolytic enzyme is trypsin.

6. The composite of claim 4 wherein the human skin is split-thickness human skin.

7. The composite of claim 1 wherein the human epidermal cells are those of a patient to be treated with the skin autograft.

8. The composite of claim 1 wherein the MCDB-153 cell culture medium is a eucaryotic cell attachment medium sufficiently devoid of alkaline earth cations to impede cell differentiation.

9. A skin autograft composite comprising viable and undifferentiated human epidermal cells attached to a sheet of collagen-coated pliable material comprising infused MCDB-153 cell culture medium.

10. The composite of claim 9 wherein the pliable material is synthetic surgical dressing.

11. The composite of claim 10 wherein the synthetic surgical dressing is defined further as comprising membranous polyurethane; polyethylene oxide and water; hydrocolloid; silicon and nylon; or monofilament nylon.

12. The composite of claim 10 wherein the synthetic surgical dressing is defined further as comprising membranous polyethylene oxide and water.

13. A skin autograft or allograft composite produced by a process comprising:
treating a synthetic surgical dressing with collagen to produce collagen-coated synthetic surgical dressing;
infusing the collagen-coated synthetic surgical dressing with eucaryotic cell medium MCDB-153;
growing human epidermal cells in a collagen-coated vessel containing eucaryotic cell medium MCDB-153 to produce undifferentiated cells;
transferring the undifferentiated human epidermal cells from the vessel to the collagen-coated synthetic surgical dressing infused with MCDB-153;
culturing the undifferentiated epidermal cells to induce attachment to the collagen-coated synthetic surgical dressing to produce a skin autograft or allograft composite consisting essentially of undifferentiated epidermal cells; and
recovering said composite.

14. The skin autograft or allograft composite of claim 13 wherein the treating step includes the steps of:
placing a sheet of synthetic surgical dressing on the lower surface of a container;
treating the placed synthetic surgical dressing with an aqueous solution of collagen and evaporating water from said solution to produce a modified collagen-coated synthetic surgical dressing.

* * * * *

UNITED STATES PATENT AND TRADEMARK OFFICE
CERTIFICATE OF CORRECTION

PATENT NO. : 5,334,527

DATED : August 2, 1994

INVENTOR(S) : Miriam M. Brysk

It is certified that error appears in the above-indentified patent and that said Letters Patent is hereby corrected as shown below:

```
   In claim 3, column 12, line 9, delete the term
"polyetehylene" and insert the word --polyethylene-- therefor.
```

Signed and Sealed this

Fourth Day of October, 1994

Attest:

BRUCE LEHMAN

Attesting Officer

Commissioner of Patents and Trademarks